United States Patent [19]

Adams

[11] 3,950,391

[45] Apr. 13, 1976

[54] ALKYL 4-(o-AMINOPHENYL)-3-THIOALLOPHA-NATES

[76] Inventor: Charles D. Adams, 12 Edgemont Road, Newark, Del. 19711

[22] Filed: Oct. 13, 1969

[21] Appl. No.: 865,964

Related U.S. Application Data

[63] Continuation-in-part of Ser. No. 805,017, March 6, 1969, which is a continuation-in-part of Ser. No. 773,302, Nov. 4, 1968, abandoned.

[52] U.S. Cl............ 260/470; 260/429 R; 260/429.9; 260/438.1; 424/287; 424/289; 424/294; 424/309
[51] Int. Cl.²............................................ C07C 157/09
[58] Field of Search ...... 260/470, 438.1, 429, 429.9

[56] References Cited

OTHER PUBLICATIONS

Tanaka et al., Chem. Abst., 66, 94930r (1967).

*Primary Examiner*—John F. Terapane

[57] ABSTRACT

Various alkyl 4-(o-aminophenyl)-3-thioallophanates and alkyl 4-(o-alkylaminophenyl)-3-thioallophanates are useful as fungicides and mite ovicides.

The compounds are prepared by reacting an o-phenylenediamine with the appropriate alkoxycarbonylisothiocyanate and an exemplary species is methyl 4-(o-aminophenyl)-3-thioallophanate.

5 Claims, No Drawings

ALKYL 4-(o-AMINOPHENYL)-3-THIOALLOPHANATES

CROSS REFERENCE TO RELATED APPLICATIONS

This application is a continuation-in-part of my copending application Ser. No. 805,017, filed Mar. 6, 1969 which is a continuation-in-part of my copending application Ser. No. 773,302, filed Nov. 4, 1968, now abandoned.

BACKGROUND OF THE INVENTION

This invention relates to a group of alkyl 4-(o-aminophenyl)-3-thioallophanates and to methods of using these compounds to prevent or mitigate damage to plants and inanimate organic materials by fungi and mites.

The survival of man has for a long time been dependent in a large measure upon his ability to protect from the various agents of destruction, plants and their products which satisfy his basic needs. With the rapidly increasing population of the world, it becomes imperative that there be continuing great improvements in the efficiency of the materials and the methods employed to provide this protection. These improvements can be in the form of effective control of more kinds of pests or in the form of requiring less material or work. The materials and methods of this invention represent marked advances in both of these possible areas of improvement, as will be explained more fully.

I have discovered that application of the compounds of this invention by the methods of this invention entirely precludes or reduces damage to plants and inanimate organic materials due to fungi and mites. Fungus mycelia are killed or prevented from developing further by the presence of one or more of the compounds, i.e., the compounds are fungicidal or fungistatic. The compounds further prevent mite populations from expanding or reduce them to a low level or even eliminate them by preventing the normal hatching of their eggs, i.e., the compounds are mite ovicides.

SUMMARY OF THE INVENTION

It has been found that the above outstanding fungicidal activity can be obtained by applying to the locus of fungus infestation, the compounds represented by the following formula:

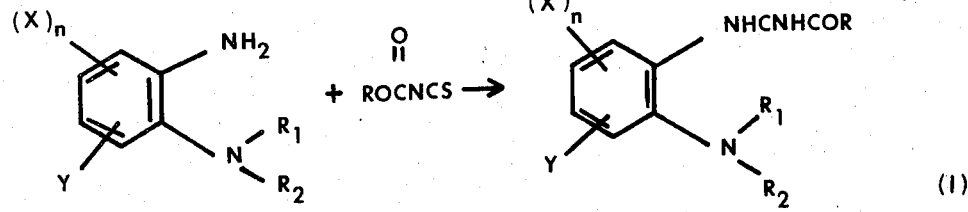

wherein
X is hydrogen, fluorine, chlorine or bromine;
Y is hydrogen or alkyl of 1 to 4 carbon atoms;
R is alkyl of 1 to 12 carbon atoms;
$R_1$ is hydrogen or alkyl of 1 to 12 carbon atoms;
$R_2$ is hydrogen or alkyl of 1 to 6 carbon atoms;
when Y is alkyl, n is 0 and when Y is hydrogen, n is 1, 2 or 3; and the sodium, potassium, lithium, calcium, barium, copper, zinc and manganese salts of these compounds.

Preferred are those compounds where X, Y, $R_1$ and $R_2$ are hydrogen and R is alkyl of 1 to 4 carbon atoms.

Particularly preferred because of their high order or fungicidal activity are: methyl 4-(o-aminophenyl)-3-thioallophanate and ethyl 4-(o-aminophenyl)-3-thioallophanate.

DETAILED DESCRIPTION OF THE INVENTION

The compounds of the invention are prepared by reacting the appropirate o-phenylenediamine with the appropriate alkoxycarbonylisothiocyanate according to the equation:

(1)

wherein
X, Y, R, $R_1$, $R_2$ and n are as previously defined.
The above reaction can be conducted in a suitable solvent, e.g. benzene, at 10°–15°C.

The sodium and potassium salts are prepared by treating a compound of formula (I) above with a sodium or potassium hydroxide in aqueous solution. The salts are isolated by evaporation of the resulting solution. The lithium salt is prepared by treating a compound of formula I with lithium hydride in methanol. The lithium salt is isolated by evaporation of the solution. The calcium, barium, copper, zinc and manganese salts are prepared from the sodium salt by treatment with the appropriate inorganic metal salt, e.g. calcium chloride. These salts are isolated by filtration. Further details on the preparation of these salts may be found in the examples.

The required alkoxycarbonylisothiocyanate is prepared according to Bull. Chem. Soc. (Japan) 36, 1214.

The required substituted o-phenylenediamines are prepared according to Montash, 33, 836; as shown by the following equation:

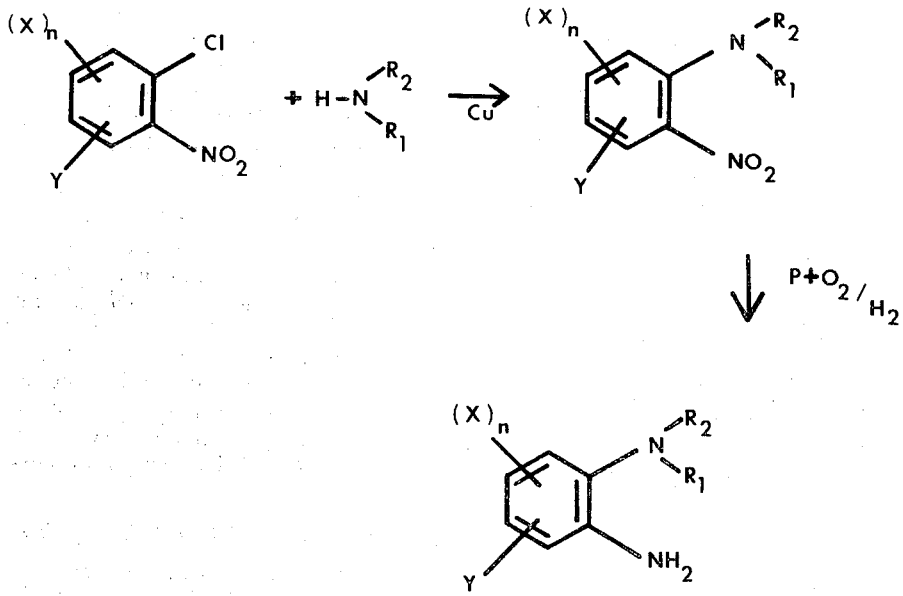

wherein

X, Y, $R_1$ and $R_2$ are as previously defined.

The general method of preparation of the compounds of this invention is illustrated by the following examples, the amounts being given in parts by weight unless otherwise specified.

EXAMPLE 1

Methyl 4-(o-Aminophenyl)-3-Thioallophanate 11.7 Parts of methoxycarbonylisothiocyanate is dissolved in 50 parts of benzene and is added to a suspension of 10.8 parts of o-phenylenediamine suspended in 200 parts of benzene at 10°–15°C. The mixture is stirred for 1 hour at room temperature and the product is then removed by filtration yielding 13.7 parts of methyl 4-(o-aminophenyl)-3-thioallophanate, m.p. 182°–183°(D). The melting point is raised to 186°–187°(D) after recrystallization from acetonitrile.

EXAMPLE 2

The following compounds (C) can be synthesized by the method of Example 1 substituting the appropriate o-phenylenediamine (A) for o-phenylenediamine and the appropriate alkoxycarbonylisothiocyanate (B), for methoxycarbonylisothiocyanate.

Compound 1
  A. o-phenylenediamine
  B. ethoxycarbonylisothiocyanate
  C. ethyl 4-(o-aminophenyl)-3-thioallophanate, m.p. 165°C.

Compound 2
  A. o-phenylenediamine
  B. isopropoxycarbonylisothiocyanate
  C. isopropyl 4-(o-aminophenyl)-3-thioallophanate Compound 3
  A. N-methyl-o-phenylenediamine
  B. methoxycarbonylisothiocyanate
  C. methyl 4-(o-methylaminophenyl)-3-thioallophanate Compound 4
  A. N-methyl-o-phenylenediamine
  B. isopropoxycarbonylisothiocyanate
  C. isopropyl 4-(o-methylaminophenyl)-3-thioallophanate Compound 5
  A. o-phenylenediamine
  B. N-hexyloxycarbonylisothiocyanate
  C. N-hexyl 4-(o-aminophenyl)-3-thioallophanate Compound 6
  A. o-phenylenediamine
  B. dodecyloxycarbonylisothiocyanate
  C. dodecyl 4-(o-aminophenyl)-3-thioallophanate Compound 7
  A. N,N-dimethyl-o-phenylenediamine
  B. methoxycarbonylisothiocyanate
  C. methyl 4-(o-dimethylaminophenyl)-3-thioallophanate The required N,N-dimethyl-o-phenylenediamine (A) can be prepared by reduction of N,N-dimethyl-o-nitroaniline with platinum oxide in ethanol.

Compound 8
  A. N-butyl-o-phenylenediamine
  B. methoxycarbonylisothiocyanate
  C. methyl 4-(o-butylaminophenyl)-3-thioallophanate The required N-butyl-o-phenylenediamine (A) is prepared by treating o-chloronitrobenzene with butylamine under pressure at 100°. The resulting N-butyl-o-nitroaniline is reduced with platinum oxide in ethanol to give N-butyl-o-phenylenediamine.

Compound 9
  A. N-dodecyl-o-phenylenediamine
  B. methoxycarbonylisothiocyanate
  C. methyl 4-(o-dodecylaminophenyl)-3-thioallophanate The N-dodecyl-o-phenylenediamine (A) is prepared by treating o-chloronitrobenzene with dodecylamine at 100° under pressure in the presence of copper powder as described in Montash, 33, 836. The resulting N-dodecyl-o-nitroaniline is reduced with platinum oxide and hydrogen to N-dodecyl-o-phenylenediamine.

Compound 10
 A. 4-chloro-o-phenylenediamine
 B. methoxycarbonylisothiocyanate
 C. methyl 4-(2-amino-4-chlorophenyl)-3-thioallophanate Compound 11
 A. 4-fluoro-o-phenylenediamine
 B. methoxycarbonylisothiocyanate
 C. methyl 4-(2-amino-4-fluorophenyl)-3-thioallophanate The 4-fluoro-o-phenylenediamine (A) is prepared by nitration of 4-fluoroacetanilide, followed by hydrolysis and reduction with platinum oxide and hydrogen.

Compound 12
 A. 4-bromo-o-phenylenediamine
 B. methoxycarbonylisothiocyanate
 C. methyl 4-(2-amino-4-bromophenyl)-3-thioallophanate The 4-bromo-o-phenylenediamine (A) is prepared by nitration of p-bromoacetanilide followed by acid hydrolysis and then reduction with platinum oxide and hydrogen.

Compound 13
 A. 4-methyl-o-phenylenediamine
 B. methoxycarbonylisothiocyanate
 C. methyl 4-(2-amino-4-methylphenyl)-3-thioallophanate Compound 14
 A. 4-butyl-o-phenylenediamine
 B. methoxycarbonylisothiocyanate
 C. methyl 4-(2-amino-4-butylphenyl)-3-thioallophanate Compound 15
 A. 4,5-dichloro-o-phenylenediamine
 B. methoxycarbonylisothiocyanate
 C. methyl 4-(2-amino-4,5-dichlorophenyl)-3-thioallophanate, m.p. 202°–203°C. (D)

EXAMPLE 3

4.5 Parts of methyl 4-(o-aminophenyl)-3-thioallophanate are dissolved in 40 parts of water containing 0.9 parts of sodium hydroxide. The sodium salt of methyl 4-(o-aminophenyl-3-thioallophonate is isolated by evaporation of the solvent at reduced pressure.

EXAMPLE 4

4.5 Parts of methyl 4-(o-aminophenyl)-3-thioallophanate are dissolved in 40 parts of water containing 1.12 parts of potassium hydroxide. The potassium salt of methyl 4-(o-aminophenyl)-3-thioallophanate is isolated by evaporation of the solvent at reduced pressure.

EXAMPLE 5

4.5 Parts of methyl 4-(o-aminophenyl)-3-thioallophanate are dissolved in 50 parts of methanol containing 0.2 parts of lithium hydride. The lithium salt of methyl 4-(o-aminophenyl-3-thioallophanate is isolated by evaporation of the solvent at reduced pressure.

EXAMPLE 6

4.5 Parts of methyl 4-(o-aminophenyl-3-thioallophanate are dissolved in 50 ml. of 5% sodium hydroxide and 4.98 parts of cupric sulfate pentahydrate dissolved in 50 parts of water are added. The cupric salt of methyl 4-(o-aminophenyl)-3-thioallophanate, 4.8 parts, is isolated by filtration, m.p. >300°C.

EXAMPLE 7

The following compounds (C) can be synthesized by the method of Example 6 substituting the appropriate alkyl 4-(o-aminophenyl)-3-thioallophanate (A) and the appropriate inorganic salt (B) for cupric sulfate pentahydrate.

Compound 1
 A. methyl 4-(o-aminophenyl)-3-thioallophanate
 B. calcium chloride dihydrate
 C. methyl 4-(o-aminophenyl)-3-thioallophanate, calcium salt Compound 2
 A. methyl 4-(o-aminophenyl)-3-thioallophanate
 B. barium chloride
 C. methyl 4-(o-aminophenyl)-3-thioallophanate, barium salt Compound 3
 A. methyl 4-(o-aminophenyl)-3-thioallophanate
 B. zinc chloride
 C. methyl 4-(o-aminophenyl)-3-thioallophanate, zinc salt Compound 4
 A. methyl 4(o-aminophenyl)-3-thioallophanate
 B. manganese II sulfate
 C. methyl 4-(o-aminophenyl)-3-thioallophanate, manganese II salt As mentioned previously, it has been found that the compounds of the invention possess outstanding fungicidal and mite ovicidal activity when employed to prevent or mitigate damage to plants and inanimate organic materials. The paragraphs which follow describe in more detail the utility of this invention.

The compounds of the invention control a wide variety of fungus diseases of foliage, fruit, stems and roots of growing plants without damage to the host. Fruits, tubers, bulbs, roots, seeds and other plant parts harvested for food, animal feed or for other purposes are protected from fungus deterioration during processing, distribution and storage. Seeds, tubers, cuttings and other plant propagation materials are protected from fungus attack during handling and storage, as well as in the soil after planting. Wood, fabric, fiber board, paper and other industrial materials are protected from unsightly stain and destructive decay caused by fungi. Luggage, shoes, shower curtains, carpets, mats, clothing and other useful household, public or industrial items are protected from rot, fungus stains and mold growth. Painted surfaces are protected from stain and discoloration by incorporation of a compound of this invention in the paint formulation.

The many fungi against which the compounds of this invention are active may be represented by, but is not intended to be limited to, the following: *Venturia inaequalis*, which causes apple scab; *Podosphaera leucotricha*, which causes powdery mildew on apple; *Uromyces phaseoli*, which causes bean rust; *Cercospora apii*, which causes early blight of celery; *Cercospora beticola*, which causes leaf spot of sugar beets; *Sclerotinia sclerotiorum*, which causes rot of vegetable crops, such as lettuce, beans, carrots, and celery; *Colletotrichum* spp., which cause anthracnose of fruits and vegetables, such as beans, tomatoes and coffee; *Septoria apii*, which causes late blight of celery; *Mycosphaerella musicola*, which causes Sigotoka disease of banana; *Piricularia* spp., which causes Johnson spot on banana; *Erysiphe cichoracearum*, which causes powdery mildew on cantaloupe and other cucurbit crops; *Penicillium digitatum, Phomopsis* spp., and *Diplodia natalensis*, which cause fruit rots on citrus; *Ceratostomella ulmi*, which causes Dutch elm disease; Sphaerotheca humuli, which causes powdery mildew on roses; *Diplocarpon rosae*, which causes black spot on roses; *Ramularia sp.*, which causes leaf spots on ornamental plants; *Botrytis cinerea*, which causes blossom and fruit rots of ornamentals, fruits and vegetables; *Uncinula necator*, which causes powdery mildew on grapes; *Guignardia bidwellii* which causes grape black rot; *Melonconium fuligineum*, which causes white rot of grapes; *Coccomyces hiemalis*, which causes cherry leaf spot; *Cytospora sp.*, which cause cankers of trees; *Cladosporium caropophilum*, which causes peach scab; Fusicladium effusum, which causes pecan scab; *Erysiphe graminis*, which causes powdery mildew on cereals; *Monolinia* (Sclerotinia) *laxa* and *M. fructicola*, which cause brown rot of stone fruits, such as peaches, cherries and apricots; *Pseudopeziza ribes*, which causes leaf spot on gooseberry; *Piricularia oryzae*, which causes rice blast; *Puccinia glumarum P. coronata* and *P. glumarum*, which cause leaf rusts of wheat, oats, and grasses, respectively; Puccinia graminis tritici, which causes stem rust of wheat; *Claviceps purpurea*, which causes ergot of rye and grasses; *Asperigillus niger*, which causes cotton boll rot as well as decay following wounding in many plant tissues; *Aspergillus flavus*, which causes mold growth on peanuts, as well as on other food and field materials; *Aspergillus terreus*, which is common in soil and attacks vegetable matter; *Tilletia caries* and other *Tilletia* species, which cause common bunt of wheat; Ustilago tritici, Ustilago nigra, Ustilago avena (and other Ustilago species), which cause loose smut of wheat, barley, and oats, respectively; *Urocystis tritici* and other *Urocystis* species, which cause loose smut of wheat; *Sphacelotheca sorghi*, which causes covered smut of sorghum; *Ustilago hordei* and *Ustilago kolleri*, which cause covered smut of barley and oats, respectively; *Pithomyces chartorum*, which is present in turf, pastures, and other grassy areas and is known to have several secondary effects; *Gloeodes pomigena*, which causes sooty blotch on apples; *Physalospora obtusa*, which causes black rot on apples; *Microthyriella rubi*, which causes flyspeck on apples; various species of *Rhizoctonia, Fusarium, Verticillium,* and *Thielaviopsis* as well as *Phytophthora parasitica* var. *nicotinae* present in soil and attacking the roots or other underground parts and the vascular system of a variety of plants; various species of *Penicillium* growing on such things as fabric, fiber board, leather goods and paint; species of *Myrothecium* attacking such items as shower curtains, carpets, mats and clothing.

The mite ovicidal action of the compounds of this invention is useful in preventing the development of damaging populations of mites or in causing the gradual reduction of existing populations. The movement of mites is limited. Thus, an increase in population or the continuation of a high population in a particular locus depends largely upon the hatching of eggs laid in that locus.

Mite eggs do not hatch to produce living young if these eggs are treated with one of these compounds, or if they are laid on a surface containing one of these compounds. Further, the eggs will not hatch if they are laid by a female mite that has been in contact with one of these compounds, or are laid by a female mite that is ingesting or has recently ingested food such as plant juices containing one of these compounds. This interference with the hatching of eggs prevents the population from increasing significantly beyond that present at the time of treatment. Also, this ovidical action, along with the high natural mortality of adults, can largely eliminate mites from an already infested area over a relatively short period of time. Further as long as the compounds are present on the surface the mites occupy or remain in their food supply, new populations cannot develop.

Many species of mites which cause damage to fruits, field crops, vegetables, and ornamentals under a wide variety of circumstances, are controlled by the compounds and methods of this invention. The extent of the practical utility of the mited control obtained is represented by, but is not intended to be limited to, the following listing of specific susceptible mites along with the types of damage that thay can cause: *Panonychus ulmi* (European red mite) and *Tetranychus telarius* (two-spotted mite) which are commonly called "orchard mites;" these mites attack a great many deciduous tree fruits including apples, pears, cherries, plums and peaches; *Tetranychus atlanticus* (Atlantic or strawberry mite), *T. cinnabarinus* (carmine spider mite) and *T. pacificus* (Pacific mite); these mites attack cotton and numerous other crop plants; *Paratetranychus citri* (citrus red mite) and others which attack citrus; *Bryobia praetiosa* (clover mite) which attacks clover, alfalfa and other crops; *Phyllocoptruta oleivora*, the citrus rust mite; *Aceria neocynodomis* which attacks grasses and other plants; *Tyrophagus lintneri* which is a serious pest in stored foods and on cultivated mushrooms and *Lepidoglyphus destructor* which injures Kentucky bluegrass seed in storage.

The compounds of this invention when applied by certain of the methods of this invention enter and move freely within plants, i.e., they are systemic. Thus both fungi and mites can be controlled in plants in parts well removed from the point of application. In view of this activity the compounds can be applied to seeds; thus the treatment of cucumber seeds with a few grams per 50 kilograms of seed of a compound of this invention provides control of powdery mildew (*Erysiphe cichoracearum*) and spider mites such as *Tetranychus urticae* on the resulting plants for periods in excess of 40 days. Applications to soil also provides control of certain foliage diseases and mites on plants growing in the treated soil. Spray or dust treatments of plant foliage and stems impart protection against both fungi and mites to other parts of the plant not actually sprayed and to new foliage developing later.

There are important practical advantages associated with the use of an effective systemic pesticide. Thus successful application to seed as described above, results in great savings in chemical and application costs. Soil applications which effectively protect entire plants for an extended period also represent similar savings. Distribution within the plant following foliage treatment eliminates the need for frequent retreatment to protect rapidly growing tissue. Also, materials within the plant are not subject to removal by rainfall. Similarly, movement or translocation of the chemical within the plant can provide protection to those parts of the plant that may not have been covered by the original spray application. This is of particular importance with plants of dense growth character resisting the intrusion of the spray and also to tall plants, such as shade trees, where the spray will not reach to the top.

An additional valuable characteristic of the compounds of this invention is their ability to prevent the spread or to kill fungus infection already established within a plant, i.e. they are curative. Thus, the compounds need not be applied until after conditions develop which permit the actual initiation of fungus attack. This means that, under some circumstances, it is possible to avoid applying any chemical during the entire life of the crop. In other cases, only a part of the normal full schedule of pesticide is required.

Therefore great savings both in chemical cost and application labor are possible with compounds capable of systemic and curative performance. Another saving is afforded by the compounds of this invention through th fact that both fungi and mites are controlled by applications of a single chemical.

The compounds of this invention provide protection from damage caused by fungi, mites or both when applied to the proper locus by the methods described hereinafter and at a sufficient rate to exert the desired fungicidal and mite ovicidal effect. The rates which will give the desired effect will be labled a pesticidally effective amount. They are especially suited for the protection of living plants such as fruit-bearing trees, nut-bearing trees, ornamental trees, forest trees, vegetable crops, horticultural crops (including ornamentals, small fruits and berries), fiber crops, grain and seed crops, sugarcane, sugar beets, pineapple, forage and hay crops, beans, peas, soybeans, peanuts, potatoes, sweetpotatoes, tobacco, hops, turf and pasture.

Living plants may be protected from fungi and mites by applying one or more of the compounds of this invention to the soil in which they are growing or in which they may subsequently be seeded or planted; or to seeds, tubers, bulbs or other plant reproductive parts prior to planting; as well as to foliage, stems and fruit of the living plant. Living plants can also be protected by dipping the root system or physically injecting the chemical or chemicals into roots or stems.

The compositions of this invention can be sprayed on to mixed into the soil. Soil applications are applied at or before planting, as a side dressing to living plants, in-therow, as a hopper-box treatment or as a soil drench. The dosage is from 2 to 100 kilograms of active ingredient per hectare treated depending on method of application and soil type.

Good results are obtained by an in-the-row treatment. Treatment is directed on a band approximately two to four inches wide over an open furrow in such a way as to strike the sides of the furrow as well as the bottom of the furrow. Seed can then be planted and the furrow closed. Alternatively, a band treatment can be used. This consists of spraying the compound on a twelve inch band and rotovating it into the soil to a depth of 15 cm. Seed may be planted in the treated bands. The seeds, seedlings and growing plants are thus protected from attack by *Rhizoctonia spp.*, *Verticillium spp.*, *Phytophthora parasitica* var. *nicotinae*, *Thielaviopsis spp.*, and *Fusarium spp.* From 0.03 to 4 kilograms of active ingredient per 4,200 meters of a 5 cm. wide row gives satisfactory protection from the fungi.

A preferred dosage in-the-row because of exceptionally good control of fungi at low cost is 0.045 to 2 kilograms of active ingredient per 4,200 meters of a 5 cm. wide row. If the band width treated is more or less two inches the dosage rate is adjusted accordingly. In-the-row treatment is extremely useful in protecting seeds, newlygerminated seedlings and growing plants of corn, cotton, tobacco, tomatoes, watermelon, squash, carrots, lettuce, sugar beets, peppers, cucumbers, beans, soybean, ornamentals and the like from attack by one or more of the above-mentioned fungi.

Soil drench treatment protect seeds, seedlings, and plants from these organisms by application of the compound used in this invention at rates of about 2 to 45 kilograms of active ingredient per acre.

Preferred rates for application to seeds, tubers, bulbs or other plant reproductive parts, range from 0.03 to 6000 grams of active compound of this invention per 50 kilograms of planting material treated. More preferred rates are in the range of 0.3 to 3000 grams of active compound per 50 kilograms. The most preferred rates are in the range of 2.8 to 1500 grams per 50 kilograms.

Applications are made from dusts, slurries or solutions. Such treatments protect the treated parts themselves from damage due to fungi, mites, or both, and in addition, impart extended protection against both types of pests to the resulting new plants.

Preferred rates for application of the compounds of this invention to foliage, stems and fruit of living plants range from 0.012 to 60 kilograms of active ingredient per hectare. More preferred rates are in the range of 0.025 to 30 kilograms per hectare and the most preferred rates are in the range of 0.05 to 15 kilograms per hectare. The optimum amount within this range depends upon a number of variables which are well known to those skilled in the art of plant protection. These variables include, but are not limited to, the disease to be controlled, weather conditions expected, the type of crop, stage of development of the crop, and the interval between applications. Applications within the range given may need to be repeated one or many times at intervals of 1 to 60 days. Applications are made from dusts, slurries or solutions.

Preferred rates for dip applications to roots of living plants are in the range of 0.5 to 18,000 grams of active ingredient per 380 liters of water or other liquid carrier. More preferred rates are in the range of 4.5 to 9,000 grams per 380 liters and the most preferred rates are in the range of 45 to 4500 grams per 380 liters.

Preferred rates for injection into the roots or stems of living plants are in the range of 0.01 to 10,000 parts per million of water or other liquid carrier. More preferred rates are in the range of 0.1 to 5,000 parts per million. The most preferred rates are in the range of 1 to 1,000 parts per million.

Plant parts such as fruits, tubers, bulbs, foliage roots and the like, harvested for food or feed, are protected from decay and other deterioration caused by fungi or mites during processing, distribution and storage by treatment with an active compound of this invention. The plant parts to be so protected can be dipped in a liquid bath containing the active ingredient, dusted with a finely divided preparation of the active ingredient, sprayed, misted with an aerosol containing the compound, or enclosed in wrapping or packing materials impregnated with the active compound.

If a liquid bath is used, it can contain an amount of the active ingredient in the range of 1 to 5,000 parts per million of the weight of the fluid. A more preferred range for the bath is 5 to 2,500 parts per million, and the most preferred range is 10 to 1,000 parts per million.

Dusts as well as wrapping or packing materials used for this type of application can contain 0.01 to 10% of the active ingredient. More preferred rates are in the range of 0.1 to 5% and the most preferred rates are in the range of 0.2 to 2.5%.

Wood, leather, fabric, fiber board, paper and other industrial materials of an organic nature can be protected from decomposition or discoloration by fungi and infestation by mites by coating, incorporating or impregnating with an effective amount of one or more of the compounds of this invention. The coating can be accomplished by dipping, spraying, flooding, misting (as with an aerosol) or dusting the material to be protected with a suitable composition containing the active ingredient. The preferred use rates for the active ingredient in the treating preparation actually applied to the material to be protected are in the range of 0.025 to 95% by weight. More preferred rates are in the range of 0.05 to 50%, with the most preferred rates being in the range of 0.1 to 25%.

Where incorporation or impregnation procedures are to be employed, use rates may be expressed in terms of the amount of active ingredient introduced into the material to be protected. The preferred use rates for these types of applications are in the range of 0.001 to 30 percent by weight of active ingredient in the final product. More preferred rates are in the range of 0.005 to 15% with the most preferred rates being in the range of 0.01 to 7%.

Luggage, shoes, shower curtains, carpets, mats, clothing and other useful household, public or industrial items are protected from rot, fungus stains and unsightly mold growth as well as infestation by mites by the active compounds of this invention. Again, either surface or deep protection can be obtained. Surface treatment is by dips, washes, sprays, aerosols or dust applications. Deep treatment is accomplished by penetrating solutions. Sprays, dips and washes contain the active compound of the invention at rates of 10 to 5000 parts per million. Fluids for aerosol application and dusts contain 0.1 to 20% by weight. Penetrating solvent solutions contain an amount of the active ingredient that results in a deposit of 5 to 20,000 parts per million in the material to be protected.

Painted surfaces can be protected from unsightly stain and mold growth by incorporating in the paint formulation, prior to application, 5 to 20,000 parts per million of an active compound of this invention. More preferred rates are in the range of 10 to 10,000 parts per million and the most preferred rates are in the range of 20 to 5,000 parts per million. Such treatments with the compounds of this invention also protect the paint while still in the can from deterioration by fungi.

Damage by mites to stored organic products such as grain, seed, bulbs, tubers, meat or animal hides is kept to a minimum by treating the floors, walls, portions, and other parts of warehouses or other structures with one or more of the active compounds. Applications are made by the use of dusts, sprays, or aerosols with preferred use rates in the range of 0.05 to 1000 grams of the active compound of this invention per 93 square meters of surface to be kept free of excessive mite populations.

As was previously set forth, the compounds of this invention are especially suited for use on living plants. Application to the foliage, stems and fruit of plants at the rate indicated above is generally accomplished by employing sprays, dusts or aerosols containing the proper amount of active ingredient. For the control of mites and fungi which are regularly present, applications often start prior to the time that the problem actually appears and continue on a pre-determined schedule. Such a procedure is termed "preventive" or "protective".

With the compounds of this invention, successful control of plant diseases can also be accomplished by applications made after they are present. Fungus mycelia within the plant tissue are actually killed. This approach or effect is termed "curative" or "eradicant" and permits the user to realize considerable savings.

Curative control of plant diseases with the compounds of this invention is enhanced if the treated plant parts are moist for one or more periods of 2 to 12 hours each soon after the active compound is applied. Often the slow drying of an original spray treatment or naturally occuring rains, mists, fogs or dews will accomplish this. Under other circumstances, such as during dry periods or in shelters such as greenhouses, it is necessary to keep the plants moist by some special effort for best results.

When the compounds of this invention are applied, their activity can be enhanced by using certain adjuvants, for example in the water in which the fungicide is dispersed. These adjuvants may be surface-active agents, oils, humectants, enzymes, carbohydrates, and organic acids. They improve the performance on tubers, on foliage, in treatments used for dip application to roots of living plants, in liquids used for injection into the roots or stems of living plants, or in mixtures used to treat fruits, tubers, bulbs, roots and the like after harvest.

The pressures of an expanding world population, together with the need for more economical agricultural practices have resulted in earlier harvesting of grains, including corn. Frequently the grain is stored or sold to grain elevators without proper drying. Spoilage of the grain under these conditions may be quite rapid, with the formation of toxins and other substances that are very harmful or fatal when fed to animals.

Safe, effective feed additives that combat spoilage are thus of great importance to agriculture.

The compounds of this invention can be used to prevent the spoilage of animal feeds. In particular, when mixed with the feed, they provide more efficient and longer lasting protection without harm or injury to livestock that consume it. The compounds of this invention may be conveniently formulated for this use in a number of the ways previously disclosed and these formulations may be mixed directly with mixed feed, newly harvested hay and newly harvested grain. These compounds effectively prevent the spoilage of corn, sorghum, wheat, barley, oats, rye and other grains that may be used as livestock feed.

Under normal conditions, these compounds may be incorporated into feeds at rates of from 0.01% to 0.25% with excellent results. Higher rates may be required under very damp conditions.

Compositions

Compositions of this invention are formulated by mixing a compound of this invention with one or more agricultural adjuvants, e.g. surface active agents.

The surface active agents used in this invention can be wetting, dispersing or emulsifying agents. They may act as wetting agents for wettable powders and dusts, as dispersing agents for wettable powders and suspension and as emulsifying agents for emulsifiable concentrates. Surfactants also enhance the biological activity of the compounds of this invention. Such surface active agents can include such anionic, cationic and nonionic agents as have heretofore been generally employed in plant control compositions of similar type. Suitable surface active agents are set out, for example, in "Detergents and Emulsifiers Annual — 1968" by John W.

McCutcheon, Inc. Other surface active agents not listed by McCutcheon but still effective dispersants by virtue of protective colloid action include methyl cellulose, polyvinyl alcohol, hydroxyethylcellulose, and alkyl substituted polyvinylpyrrolidones.

Suitable surface active agents for use in compositions of this invention include polyethylene glycol esters with fatty and rosin acids, polyethylene glycol ethers with alkyl phenols or with long-chain aliphatic alcohols, polyethylene glycol ethers with sorbitan fatty acid esters, and polyoxyethylenethio ethers. Other suitable surfactants include amino, alkali and alkaline earth salts of alkyl aryl sulfonic acids, amine, alkali and alkaline earth fatty alcohol sulfates, dialkyl esters of alkali metal sulfosuccinates, fatty acid esters of amine, alkali and alkaline earth isethionates and taurates, amine, alkali and alkaline earth salts of lignin sulfonic acids, methylated or hydroxyethylated cellulose, polyvinyl alcohols, alkyl substituted polyvinylpyrrolidone, amine, alkali and alkaline earth salts of polymerized alkylnaphthalene sulfonic acids, and long-chain quaternary ammonium compounds. Anionic and nonionic surface active agents are preferred.

Among preferred wetting agents are sodium alkyl naphthalene sulfonates, sodium dioctylsulfosuccinate, sodium dodecylbenzene sulfonate, ethylene oxide condensates with alkylated phenols such as octyl, nonyl and dodecyl phenol, sodium lauryl sulfate, and trimethylnonyl polyethylene glycols. Among preferred dispersing agents are sodium, calcium and magnesium lignin sulfonates, low-viscosity methyl cellulose, low-viscosity polyvinyl alcohol, alkylated polyvinylpyrrolidone, polymerized alkyl naphthalene sulfonates, sodium N-oleyl or N-lauroye isethionates, sodium N-methyl-N-palmitoyl taurate and dodecylphenol polyethylene glycol esters.

Among preferred emulsifying agents are ethylene oxide adducts of lauric, oleic, palmitic, or stearic acid esters of sorbitan or sorbitol, polyethylene glycol esters with lauric, oleic, palmitic, stearic or rosin acids, oil-soluble alkylarylsulfonates, oil-soluble polyoxyethylene ethers with octyl, nonyl and dodecylphenol, polyoxyethylene adducts to long-chain mercaptans, and mixtures of these surfactants.

In general, less than 10% by weight of the surfaceactive agent will be used in compositions of this invention and ordinarily the amount of surface-active agents will range from 1–5% but may even be less than 1% by weight.

Additional surface-active agents can be added to the above formulation to increase the ratio of surfaceactive agent: active agent up to as high as 5:1 by weight. Normally the purpose of adding higher amounts of surfactant is to increase the fungicidal effect of the active compounds. When used at higher rates it is preferred that the surfactant be present in the range of one-fifth to five parts surfactant for each one part of active agent.

Compositions of this invention will contain, in addition to surface active agents other agricultural adjuvants such as solid or liquid diluents to produce wettable powders, dusts, granules or emulsifiable liguids as desired.

A. Wettable Powders

Wettable powders are compositions which usually contain inert solid diluents in addition to surfactants. These inert diluents may serve several purposes. They can act as grinding aids to prevent mill smear and screen blinding, they can aid rapid dispersion of the mix when placed in water, they can adsorb liquid or low melting solid active material to produce a free flowing solid product, they can prevent agglomeration into lumps upon prolonged hot storage and they can permit preparation of compositions with a controlled amount of active ingredient so that proper dosage is easily measured by the consumer.

Suitable diluents may be either inorganic or organic in origin. These include the natural clays, diatomaceous earth, synthetic mineral fillers derived from silica or silicates, insoluble salts produced by precipitation in fluffy form such as tricalcium phosphate or calcium carbonate, and powdered organic diluents such as shell flours, corn cob flour or sucrose. Preferred fillers for the compositions of this invention include kaolin clays, attapulgite clay, nonswelling calcium magnesium montmorillonites, synthetic silicas, synthetic calcium and magnesium silicates, diatomaceous silica, corn cob flour and sucrose.

Wettable powders will normally contain both a wetter and a dispersant. Most preferred for dry wettable powders are those anionic and nonionic surfactants which exist in solid form. Occasionally a liquid, nonionic surfactant, normally considered and emulsifying agent can be used to produce both wetting and dispersion.

Wetting and dispersing agents in wettable powders of this invention, when taken together, will comprise from about 0.5 weight percent to 5.0 weight percent of the total composition. The active component will be present at a concentration of from about 25% to 80% and diluent makes up the balance to 100%. Where needed a corrosion inhibitor or foaming inhibitor may be added at rates of 0.1% to 1.0% with a corresponding reduction in diluent.

B. Dusts

Dust compositions are those intended for application in dry form with suitable dusting equipment. Since wind drift is undesirable when applying dusts, the most suitable dust diluents are those which are dense and rapid settling. These include kaolinites, talcs, pyrophyllities, ground phosphate rock, Serecite, and ground tobacco stems. However, dusts are usually most easily prepared by diluting an existing high-strength wettable powder with a diluent so that the final dust will frequently contain a fraction of light, absorptive diluent as well as a denser filler.

A wetting agent is desirable in dust formulations so that adhesion to dew-covered foliage is enhanced. Dusts made from wettable powders will usually contain sufficient wetter, but dusts made directly from unformulated active will usually contain an added wetting agent. Dry solid anionic or nonionic wetters are preferred.

Dust formulations will normally contain from 5.0 weight percent to 25 weight percent of active material, from 0.005% to 1.0% wetting agent, and from 3% to 20% light grinding aid diluent and the balance dense, rapid settling diluents. If made by diluting a prepared wettable powder, it will also contain a small amount of dispersing agent which has no active role when the composition is used as a dry dust.

C. Emulsifiable Liquids

Emulsifiable liquids are formulated by combining the compounds of this invention with a suitable emulsifier and an organic liquid with low water solubility. The active component may be completely dissolved in the organic liquid or it may be a finely ground suspension in a nonsolvent liquid. Suitable organic liquids include alkylated naphthalenes, xylene, high molecular weight ketones, such as isophorones, dibutyl or diamyl ketone, esters such as amyl acetate and normal or oil soluble sulfonates and nonionic polyoxyethylene glycol esters or ethers of fatty acids or alkylated phenols.

The active component in emulsifiable concentrates will be present at from 10 weight percent to about 40 weight percent. Combined emulsifiers will be present at from 3 weight percent to about 10 weight percent and the balance will be an organic carrier liquid or solvent.

D. Granules

Soil treatments with fungicides, either pre-or post-emergence can frequently be most readily applied with granules. Granular products, with the compounds of this invention, can be made in a number of ways. The active materials can be melted or dissolved in a volatile carrier and sprayed upon preformed granules. They may be mixed as powders with suitable diluents and binders, then moistened and granulated followed by drying. Powders may also be applied to coarsely porous granules by tumbling together and applying some nonvolatile liquid such as oil, glycol or a liquid non-ionic surfactant to act as a binder. Rates of granule disintegration and dispersion of active material in moist soil can be controlled by choice of added surfactants or selection of the binder used to form the granule.

Suitable preformed granules include those made from attapulgite clay, granular expanded vermiculite, ground corn cobs, ground nut shells or preformed kaolinite granules. When active fungicide is placed upon such carriers the concentration may range from 1% to 25%. However, unless applied from a molten state, it is difficult to prevent segregation of active and carrier in concentration ranges above 10% on preformed granules. When higher concentrations of active are desired best results are obtained by premixing powdered active, diluents, binders and surfactants, then granulating so that the active is distributed throughout the granule and not solely upon its surface.

Suitable diluents for the preparation of granules by granulation or extrusion include kaolin clays, sucrose nonswelling Ca, Mg montmorillonites, and gypsum. Cohesion to a firm granule is usually obtained by moistening, compacting and drying, with or without some binding agent. Kaolin clays form firm granules if bound together with gelatinous agents such as methylcellulose, natural gums or swelling bentonite. Calcium-magnesium bentonites require no binder and gypsum can be made to form firm granules with either the addition of plaster of Paris or certain salts such as ammonium sulfate, potassium sulfate or urea which form double salts with gypsum.

The active content of formed granules can range from 1–90% although 75% active represents about the upper level if controlled disintegration of the granule in moist soil is desired. Control of disintegration rate is attained by controlled compaction, e.g., controlled extrusion pressure or by the addition of inert water-soluble components such as sodium sulfate or sugar which can leach away.

E. Aqueous Dispersons

Aqueous dispersions of fungicides may be preferred to wettable powders where minimum agitation is available in application equipment and accurate dosage is essential. Even the best and finest wettable powder will not disperse completely in water. Small agglomerates remain which settle rapidly. However, when a solid is ground in a water phase, in the presence of dissolved surfactants, each particle develops an adsorbed layer that repels its neighbors and complete dispersion is maintained. This will still not prevent a slow settling to the bottom of stored containers with the formation of a dense "clay" that is difficult to resuspend. A practical aqueous dispersion concentrate must be free from "claying" during an extended shelf life. Certain acrylic acid polymers and sheared hydrated attapulgite will effectively prevent claying.

Suitable aqueous dispersion of the compounds of this invention are prepared by pebble milling or sand milling the active ingredient, one or more dispersants and an anticlaying component in water until the active particle size is less than 10 microns, preferably less than 5 microns. In climates where freezing is a problem, mixtures of glycols and water may be used as a continuous phase.

Low Volume Applications

While conventional applications of sprayable formulations have usually been made in a dilute form (for example at a rate of about 200 liters per hectare or more), the compounds of this invention can also be applied at higher concentrations in the typical "ultra-low-volume" or "low-volume" applications from aircraft or ground sprayers. For this purpose wettable powders can be dispersed in small amounts of aqueous or non-aqueous carriers and the suspension for emulsifiable concentrates can be used directly or with minor dilution. Special compositions, particularly suitable for ULV applications and solutions or finely divided suspensions in one or more carriers such as dialkylformamides, N-alkylpyrrolidones, dimethylsulfoxide, water esters, ketones, glycols, glycol ethers and the like. Other suitable carriers include aromatic hydrocarbons (halogenated and non-halogenated), aliphatic hydrocarbons (halogenated and non-halogenated) and the like.

The compositions of the invention can contain, in addition to the active ingredient of this invention, conventional insecticides, miticides, bactericides, nematocides, fungicides, or other agricultural chemicals such as fruit set agents, fruit thinning compounds, fertilizer ingredients and the like, so that the compositions can serve useful purposes in addition to the control of fungi and mite infestations.

The following are illustrative of the agricultural chemicals that can be included in the compositions or, additionally, that may be added to sprays containing one or more of the active compounds.

The additional agricultural chemicals are employed in mixtures or combinations in amounts ranging from one-fifth to twenty times that of the compound or compounds of this invention. The proper choice of amounts is readily made by one skilled in the art of protecting plants from pest depredations.

1,2,3,4,10,10-hexachloro-1,4,4a,5,8,8a-hexahydro-1,4-endoexo-5,8-dimethanonaphthalene (aldrin);

1,2,3,4,5,6-hexachlorocyclohexane (lindane);

2,3,4,5,6,7,8,8-octachloro-4,7-methano-3a-4,7,7a-tetrahydroindane;

1,1,1-trichloro-2,2-bis(p-chlorophenyl)ethane (DDT);

1,2,3,4,10,10-hexachloro-6,7-epoxy-1,4,4a-5,6,7,8,8a-octahydro-1,4-endo-exo-5,8-dimethanonaphthalene (dieldrin);

1,2,3,4,10,10-hexachloro-6,7-epoxy-1,4,4a,5,6,7,8,8a-octahydro-1,4-endo-endo-5,6-dimethanonaphthalene (endrin);

1 (or 3a), 4,5,6,6,8,8-heptachloro-3a-4,7,7a-tetrahydro-4,7-methanoindene;
1,1,1-trichloro-2,2-bis(p-methoxyphenyl)ethane (methoxychlor);
1,1-dichloro-2,2-bis(p-chlorophenyl)ethane;
chlorinated camphene having a chlorine content of 67–69%;
2-nitro-1,1-bis(p-chlorophenyl)butane;
1-naphthyl-N-methylcarbamate ("Sevin");
methylcarbamic acid, ester with phenol, 4-(dimethylamino)-3,5-dimethyl;
methylcarbamic acid, ester with 1,3-dithiolan-2-one oxime; O,O-diethyl-O-(2-isopropyl-4-methylpyrimid-6-yl)thiophosphate;
O,O-dimethyl-1-hydroxy-2,2,2-trichloroethyl phosphonate;
O,O-dimethyl-S-(1,2-dicarbethoxyethyl)dithiophosphate (malathion);
O,O-dimethyl-O-p-nitrophenyl thiophosphate (methyl parathion);
O,O-dimethyl-O-(3-chloro-4-nitrophenyl)thiophosphate;
O,O-diethyl-O-p-nitrophenyl thiophosphate (parathion);
dl-2cyclopentenyl-4-hydroxy-3-methyl-2-cyclopenten-1-one chrysanthemate;
O,O-dimethyl-O-(2,2-dichlorovinyl)phosphate (DDVP); mixture containing 53.3% "Bulan", 26.7% "Prolan" and 20.0% related compounds;
O,O-dimethyl-O-(2,4,5-trichlorophenyl)phosphorothioate;
O,O-dimethyl-S-(4-oxo-1,2,3-benzotriazine-3(4H)-ylmethyl)-phosphorodithioate ("Guthion");
bis(dimethylamino)phosphonous anhydride;
O,O-diethyl-O-(2-keto-4methyl-7a'-pyranyl)thiophosphate;
O,O-diethyl (S-ethyl mercaptomethyl)dithiophosphate;
calcium arsenate;
sodium aluminofluoride; dibasic lead arsenate;
2'-chloroethyl-1-methyl-2-(-tert-butylphenoxy)ethyl sulfite; azobenzene;
ethyl 2-hydroxy-2,2-bis(4-chlorophenyl)acetate;
O,O-diethyl-O-(2(ethylmercapto)-ethyl)thiophosphate;
2,4-dinitro-6-sec-butyl phenol;
toxaphene;
O-ethyl-O-p-nitrophenylbenzenethiophosphonate;
4-chlorophenyl-4-chlorobenzene sulfonate;
p-chlorophenyl-phenyl sulfone;
tetraethyl pyrophosphate;
1,1bis(p-chlorophenyl)ethanol;
1,1-bis(chlorophenyl)-2,2,2-trichloroethanol;
p-chlorophenyl-p-chlorobenzyl sulfide;
bis(p-chlorophenoxy)methane;
3-(1-methyl-2-pyrrolidyl)pyridine;
mixed ester of pyrethrolone and cinerolone ketoalcohols and two chyrsanthemum acids;
cube and derris, both whole root and powdered;
ryanodine;
mixture of alkaloids known as veratrine;
dl-2-allyl-4-hydroxy-3-methyl-2-cyclopenten-1-one esterified with a mixture of cis and trans dl-chrysanthemum monocarboxylic acids;
butoxypolypropylene glycol;
p-dichlorobenzene;
2-butoxy-2'-thiocyanodiethyl ether;
naphthalene;
methyl 0-carbamylthiolacetohydroxamate; 1,1-dichloro-2,2-bis(p-ethylphenyl)ethane;
methyl 0-(methylcarbamoyl)thiolacetohydroxamate;
p-dimethylaminobenzenediazo sodium sulfonate;
quinone oxyaminobenzooxohydrazone;
tetraalkyl thiuram disulfides such as tetramethyl thiuram; disulfide or tetraethyl thiuram disulfide;
metal salts of ethylene bisdithiocarbamic acid, e.g. manganese, zinc, iron and sodium salts; sulfur;
pentachloronitrobenzene;
N-dodecylguanidine acetate (dodine);
N-trichloromethylthiotetrahydrophthalimide (captan);
phenylmercury acetate;
2,4-dichloro-6-(o-chloroaniline)-s-triazine ("Dyrene");
N-methylmercury p-totuenesulfonanilide;
chlorophenolmercury hydroxides;
nitrophenolmercury hydroxides;
ethylmercury acetate;
ethylmercury 2,3-dihydroxypropyl mercaptide;
methylmercury acetate;
methylmercury 2,3-dihydroxypropyl mercaptide;
3,3'-ethylenebis(tetrahydro-4,4-dimethyl-2H-1,3,5-thiodiazine-2-thione);
methylmercury dicyandiamide;
N-ethylmercury-p-toluenesulfonilide;
1,4-dichloro-2,5-dimethoxy benzene; metal (e.g. iron, sodium and zinc), ammonium and amine salts of dialkyl dithiocarbamic acids;
tetrachloronitroanisole;
hexachlorobenzene;
hexachlorophene;
methylmercury nitrile;
tetrachloroquinine;
N-trichloromethylthiophthalimide;
1,2-dibromo-3-chloropene; 1,2-dibromo-3-chloroprene;
dichloropropane - dichloropropene mixture;
ethylene dibromide;
chloropicrin;
sodium dimethyl dithiocarbamate;
tetrachloroisophthalonitrile;
1-benzimidazole carboxylic acid, 2-carboxyaminodimethyl ester streptomycin;
2-(2,4,5-trichlorophenoxy)propionic acid;
p-chlorophenoxyacetic acid;
1-naphthaleneacetamide; and
N-(1-naphthyl)acetamide.

The agricultural chemicals listed above are merely exemplary of the compounds which can be mixed with the active compounds and are not intended to any way limit the invention.

The use of pesticides such as those listed above in combination with a compound within the scope of this invention sometimes appears to greatly enhance the activity of the active compound. In other words, an unexpected degree of activity is sometimes seen when another pesticide is used along with the active compound.

In order that the invention may be better understood, the following examples are given in addition to those above. All parts are parts by weight unless otherwise indicated.

Wettable Powders

EXAMPLE 8

| | Percent |
|---|---|
| Methyl 4-(o-aminophenyl)-3-thioallophanate | 50 |
| alkylnaphthalenesulfonic acid, sodium salt | 1 |
| low viscosity methyl cellulose | 0.5 |
| Kaolin clay | 48.5 |

The ingredients are combined, mixed, micropulverized, air milled and then blended. The resulting powder wets and disperses readily in water and is suitable for application in normal spray equipment.

The above 50% wettable powder formulation is dispersed in water to give an active ingredient concentration of 300 ppm in water. Eight uniform apple trees of the same variety are selected for testing. Four of these are sprayed to run-off, which is approximately 2,850 liters per hectare, at weekly intervals during the growing season with the above formulation, and the other four trees are left unsprayed.

By the end of the season the unsprayed trees are highly infected with apple scab, Venturia inaequalis. They have poor twig growth and small, spotted fruit. The trees sprayed with the formulation of this example are essentially free of scab disease have a foliage of a thrifty, dark green color, and exhibit good twig growth and fruit size.

EXAMPLE 9

The wettable powder of Example 8 is rotovated into soil in a 30 cm. band 15 cm deep infested with soil fungi such as *Fusarium oxysporum f. vasinfectum*. The rate used in thirty four kilograms per hectare of active ingredient. Cotton seeds are planted and subsequently grow and produce an acceptable crop of cotton. Cotton seed planted in untreated soil germinate but the seedlings and growing plants are infected with this wilt organism resulting in substantially reduced yields.

EXAMPLE 10

|  | Percent |
|---|---|
| Ethyl 4-(o-aminophenyl)-3-thio-allophanate | 60 |
| dialkylsulfosuccinate, sodium salt | 1 |
| sodium ligninsulfonate | 1 |
| diatomaceous silica | 38 |

The materials are combined, air milled twice, and then blended.

The formulation of this example is useful for the control of peach scab and brown rot caused by the fungi, *Cladosporium carpophilum* and *Monolinia laxa*. This is demonstrated by an orchard study in which random trees in a peach planting are sprayed to run off. Starting in the spring selected trees are sprayed from all sides with the formulation of this example at a rate of 300 ppm active ingredient in water. The same trees are sprayed each 14 days throughout the season. At harvest the trees receiving the treatment are heavily laden with large healthy peaches. On the other hand, the trees which did not receive the treatment had only a few fruit because of a severe blossom blight infection with brown rot, and those remaining fruit were severely spotted with scab lesions.

The following compounds can be substituted one at a time for the ethyl 4-(o-aminophenyl)-3-thioallophanate above in like amount by weight. They are formulated and applied in like manner and like results are obtained.
methyl 4-(o-dimethylaminophenyl)-3-thioallophanate
methyl 4-(o-butylaminophenyl)-3-thioallophanate
isopropyl 4-(o-methylaminophenyl)-3-thioallophanate
methyl 4-(o-aminophenyl)-3-thioallophanate

EXAMPLE 11

This wettable powder of Example 10 is rotovated into soil in a 30 cm band 15 cm deep infected with *Verticillium albo-atrum*. The rate used is twenty eight kilograms per hectare of active ingredient. Cotton seeds are planted and subsequently grow and produce an acceptable crop of cotton. Cotton seed planted in untreated soil germinate but the seedlings and growing plants are infected with this wilt organism resulting in substantially reduced yields.

EXAMPLE 12

|  | Percent |
|---|---|
| isopropyl 4-(o-methylaminophenyl)-3-thioallophanate | 50 |
| alkylbenzenesulfonic acid, sodium salt | 1 |
| sodium ligninsulfonate | 1 |
| diatomaceous silica | 48 |

The materials are combined, micropulverized, air milled, and then blended.

A uniform field planting of cantaloupe in North Carolina is inoculated with the powdery mildew fungus (*Erysiphe cichoracearum*). After 10 days this organism has become well established in the plants.

At this time alternate rows are sprayed with water containing a suspension of the wettable powder prepared as described above and an added amount of a polyhydric alcohol ester surface-active agent ("Trem" 014). The concentration of this chemical suspension is such as to give 227 grams of the active compound of this formulation per 378 liters of water (600 ppm) and 400 ppm of the surfactant. The spray is applied at a volume of 1400 liters per hectare. The remaining rows are left unsprayed.

After another 15 days the unsprayed rows are heavily damaged by powdery mildew and some of the plants are dying. The sprayed rows, however, are healthy and growing rapidly. The results indicate that the active compound of the suspension acts as a curative fungicide.

EXAMPLE 13

|  | Percent |
|---|---|
| Methyl 4-(o-aminophenyl)-3-thioallophanate | 70 |
| sucrose + impurities in technical active material | 26.5 |
| dioctylsulfosuccinate, sodium salt | 3 |
| low viscosity methyl cellulose | 0.5 |

The materials are combined, micropulverized, air milled and then blended.

Test plots are established in a rice field. The plots are sprayed with water containing a suspension of the wettable powder described above along with a polyhydric alcohol ester surface active agent (Trem 014). The amount of the wettable powder used is such as to provide 0.6 grams of the active compound of this invention per liter of water (600 ppm). The amount of Trem 014 is 400 ppm in the final spray. The spray is applied at weekly intervals at the rate of 900 liters per hectare. The remainder of the field is left unsprayed. Three months after the start of the test, the sprayed plots are healthy and growing well. The untreated plots, on the other hand, are seriously damaged by the rice blast fungus, *Piricularia oryzae* which greatly reduces yield.

The following compounds are each substituted one at a time for the methyl 4-(o-aminophenyl)-3-thioallophanate above in like amount by weight. Each is formulated, applied in like manner and similar results are obtained.
ethyl 4-(o-aminophenyl)-3-thioallophanate,
methyl 4-(o-dimethylaminophenyl)-3-thioallophanate
methyl 4-(o-butylaminophenyl)-3-thioallophanate
isopropyl 4-(o-methylaminophenyl)-3-thioallophanate

EXAMPLE 14

This wettable powder of Example 13 is mixed with water and rotovated into a 30 cm band of soil 15 cm deep infected with the black rot fungus *Thielaviopsis basicola*. The rate used is twenty two kilograms per hectare of active ingredient in the band. Tobacco seedlings planted in the treated soil are protected from attack by the fungus, resulting in a healthy crop. Tobacco plants planted in untreated soil grow poorly or are killed resulting in less yield than from tobacco grown in treated soil.

EXAMPLE 15

|  | Percent |
|---|---|
| methyl 4-(o-dimethylaminophenyl)-3-thioallophanate | 5 |
| Kaolin | 5 |
| Sodium dialkylsulfosuccinate | 0.5 |
| Talc | 89.5 |

The active material, surfactant and kaolin are combined and ground and then mixed with the talc and blended.

A single row is selected in a sugar beet field for treatment with the dust of this formulation. After the sugar beets are one month old and a few lesions of *Cercospora beticola* have become evident as spots on the leaves, weekly dust treatments are applied to the selected row. The 5% dust of this formulation is applied to a single row at approximately 30 kilograms per hectare. There is some drift to adjacent rows but the remainder of the field is left untreated. At harvest the foliage is examined and the beets are dug and weighed. The treated row is a vigorous healthy row with lush green foliage and the beets are large and normal. The adjacent rows are spotted with numerous leaf spot lesions and the remainder of the field is almost entirely defoliated. A few young leaves on the untreated beets are still green but all of the other leaves are dried up. Beets from the untreated rows are less than half normal size.

Any of the compounds of this invention can be formulated in like manner and applied with similar results.

EXAMPLE 16

|  | Percent |
|---|---|
| Wettable powder of Example 8 | 6 |
| micaceous talc | 94 |

The above ingredients are blended to give a freely flowing dust.

This dust formulation is applied to individual vines of grapes in otherwise untreated rows in a vineyard. The applications are made at a rate of twenty kilograms per hectare at 14 day intervals for a period of three months during the growing season. At the end of the treatment period, the treated vines are healthy, support a heavy crop of high quality fruit, and show evidence of excellent cane growth. The foliage and fruit of untreated vines are severly damaged by powdery mildew (*Uncinula necator*) and by *Botrytis* and other fruit rots.

Any of the wettable powders of Examples 9-14, incl., can be substituted for the above wettable powder and applied with similar results.

Granules

EXAMPLE 17

|  | Percent |
|---|---|
| Methyl 4-(o-aminophenyl)-3-thioallophanate | 20 |
| Attapulgite clay | 6 |
| calcium, magnesium bentonite | 66 |
| anhydrous sodium sulfate | 8 |

The powdered active material and other ingredients are combined and moist granulated, dried and then screened to make a 20-80 mesh mixture.

A field in California is seeded with cotton in the normal manner, except that granules prepared as set forth above are added to alternate rows. These granules are dropped in such a way that some fall into the furrow and some are mixed with the covering soil. The rate of granule application is such as to employ 1.0 kilograms of active chemical of this invention per 4200 meters of row. The remaining rows are untreated.

Six weeks after planting, many of the plants in the rows without the granules are dead, and others shown soreshin lesions caused by *Rhizoctonia solani*.

Pellets

EXAMPLE 18

|  | Percent |
|---|---|
| Methyl 4-(o-butylaminophenyl)-3-thioallophanate | 25 |
| calcium, magnesium bentonite | 64 |
| sodium sulfate, anhydrous | 10 |
| alkylnaphthalenesulfonic acid, sodium salt | 1 |

This composition is blended, moistened with water in a pug mill and then extruded and dried.

The pellets of this example may be applied in a manner similar to the granules of Example 17 with comparable results.

Aqueous Dispersion

EXAMPLE 19

|  | Percent |
|---|---|
| Methyl 4-(o-aminophenyl)-3-thioallophanate | 30 |
| calcium, magnesium ligninsulfonate (goulac) | 15 |
| attapulgite, hydrated | 3 |
| disodium phosphate, anhydrous | 1 |
| dodecyl alcohol | 0.005 |
| water | 50.995 |

The dispersion is prepared by mixing the ingredients and sand milling the mixture.

Six field crates of oranges are picked from a commercial grove in Florida. Three of these crates of oranges are dipped for 3 minutes in a water bath containing a suspension made from the above formulation, in an amount to give 300 parts per million by weight of the active ingredient of this invention. A polyethylene glycol ester of oleic acid surface active agent is present at the rate of 150 ppm of total liquid. The remaining three crates are dipped in a similar fashion in water with the surface-active agent only. All crates are set aside in a citrus storage house for three weeks. At the end of this time all fruits are examined. The fruit that has been dip-treated with the compounds of this invention is still in good condition, but the fruit that is not so protected is largely rotted by the green mold fungus (*Penicillium digitatum*).

The other compounds of this invention may be similarly formulated and when used as above give like results.

Oil Dispersion

EXAMPLE 20

|  | Percent |
|---|---|
| Ethyl 4-(o-aminophenyl)-3-thioallophanate | 25 |
| blend of polyalcohol carboxylic acid esters and sulfonated oils | 8 |
| isoparaffin oils (Soltrol 170) | 67 |

The dispersion is prepared by mixing the ingredients and sandmilling the mixture. The resulting dispersion can be sprayed as a concentrate, diluted with oil or emulsified in water and then applied.

The formulation of this example is useful for the control of the Sigatoka disease fungus (*Mycosphaerella musicola*). This is demonstrated by a plantation study in which a plot showing the first visible yellow spots of the disease is sprayed from the air with an aqueous suspension of this formulation containing 10,000 ppm active ingredient at a rate of 454 grams in 45 liters of water per hectare. The adjacent plots, also showing signs of incipient disease, are left untreated. At harvest the foliage is examined and representative samples of fruit weighed. The untreated plots show severely damaged leaves and prematurely ripened, small, unmarketable bananas. The treated plot yields heavy well developed bananas from vigorous undiseased plants.

The following compounds may be substituted one at a time for the ethyl 4(o-aminophenyl)-3-thioallophanate above in a like amount by weight. When formulated and applied in like manner, similar results are obtained.

methyl 4-(o-aminophenyl)-3-thioallophanate
methyl 4-(o-dimethylaminophenyl)-3-thioallophanate
methyl 4-(o-butylaminophenyl)-3-thioallophanate
isopropyl 4-(o-methylaminophenyl)-3-thioallophanate

EXAMPLE 21

The formulation of Example 20 is emulsified in water and sprayed in an open furrow at four and one-half kilogram per hectare of active ingredient. Cucumber seeds are planted in the treated furrow at the same time as the treatment is made and the furrow closed. The cucumber seeds germinate and the seedlings and growing plant are protected from attack by the fungus *Rhizoctonia solani* resulting in a healthy stand and good crop of beans. Bean seeds planted in untreated soil are essentially destroyed and the few plants that remain are severely diseased and produce a poor crop.

Example 22

|  | Percent |
|---|---|
| Isopropyl 4-(o-methylaminophenyl)-3-thioallophanate | 10 |
| blend of polyalcohol carboxylic acid esters and sulfonated oils | 6 |
| isophorone | 84 |

The above ingredients are mixed until all active material has dissolved. The resulting solution can be sprayed as a concentrate, extended with additional solvent, or emulsified in water before application.

The formulation of this example is useful for the control of the Sigatoka disease fungus (*Mycosphaerella musicola*). This is demonstrated by a plantation study in which a plot showing the first visible yellow spots of the disease is sprayed from the air with an aqueous suspension of this formulation containing 454 grams of active ingredient in 45 liters of water per hectare. The adjacent plots, also showing signs of incipient disease, are left untreated. At harvest the foliage is examined and representative samples of fruit weighed. The untreated plots show severely damaged leaves and prematurely ripened, small, unmarketable bananas. The treated plot yields heavy well developed bananas from vigorous undiseased plants.

The following compounds may be substituted one at a time for the isopropyl 4-(o-methylaminophenyl)-3-thioallophanate above in like amount by weight. When formulated and applied in like manner, like results are obtained.

methyl 4-(o-aminophenyl)-3-thioallophanate
ethyl 4-(o-aminophenyl)-3-thioallophanate
methyl 4-(o-dimethylaminophenyl)-3-thioallophanate
methyl 4-(o-butylaminophenyl)-3-thioallophanate

EXAMPLE 23

The formulation of Example 22 is emulsified in water and sprayed in an open furrow at one kilogram per hectare of active ingredient. Bean seeds are planted in the treated furrow at the same time as the treatment is made and the furrow closed. The bean seeds germinate and the seedlings and growing plant are protected from attack by the fungus *Rhizoctonia solani* resulting in a healthy stand and good crop of beans. Bean seeds planted in untreated soil are essentially destroyed and the few plants that remain are severely diseased and produce a poor crop.

EXAMPLE 24

|  | Percent |
|---|---|
| Methyl 4-(o-aminophenyl)-3-thioallophanate | 50 |
| alkylnaphthalenesulfonic acid, sodium salt | 1 |
| low viscosity methyl cellulose | 0.5 |
| Kaolin clay | 48.5 |

The ingredients are combined, mixed, micropulverized, air milled and then blended. The resulting powder wets and disperses readily in water and is suitable for application in normal spray equipment.

The above 50% wettable powder formulation is dispersed in water to give an active ingredient concentration of 4000 ppm in water. Eight uniform apple trees of the same variety are selected for testing. Four of these are sprayed to run-off, which is approximately 2850 liters per hectare, at weekly intervals during the growing season with the above formulation, and the other four trees are left unsprayed.

By the end of the season the unsprayed trees have developed very high populations of orchard mites and are highly infected with apple scab, *Venturia inaequalis*. Due to the feeding of the mites, the foliage is russeted and drops prematurely. Also the untreated trees have poor twig growth and small, spotted fruit. The trees sprayed with the formulation of this example are essentially free of mites, their eggs and apple scab disease. As a result of the excellent mite control, the sprayed trees have foliage of a thrifty, dark green color, and they exhibit good twig growth and fruit size.

I claim:
1. A compound of the formula:

$$\text{Y}\underset{(X)_n}{\underset{|}{\bigcirc}}\overset{\text{NHCNHCOR}}{\underset{\text{N}\overset{R_1}{\underset{R_2}{}}}{}}\quad\overset{S\quad O}{\overset{\|\quad\|}{}}$$

wherein
X is hydrogen, fluorine, chlorine, or bromine;
Y is hydrogen or alkyl of 1 to 4 carbon atoms;
R is alkyl of 1 to 12 carbon atoms;
$R_1$ is hydrogen or alkyl of 1 to 12 carbon atoms;
$R_2$ is hydrogen or alkyl of 1 to 6 carbon atoms;
when Y is alkyl, n is 0 and when Y is hydrogen, n is 1, 2 or 3; and the sodium, potassium, lithium, calcium, barium, copper, zinc and manganese salts of these compounds.

2. A compound of the formula:

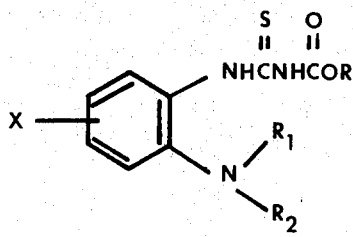

wherein
X is hydrogen, fluorine, chlorine, bromine or alkyl of 1–4 carbon atoms,
R is alkyl of 1–12 carbon atoms;
$R_1$ is hydrogen or alkyl of 1–12 carbon atoms, and $R_2$ is hydrogen or alkyl of 1–6 carbon atoms.

3. The compound of claim 1 wherein X, Y, $R_1$ and $R_2$ are hydrogen and R is alkyl of 1 to 4 carbon atoms.

4. The compound of claim 1 which is methyl 4-(o-aminophenyl)-3-thioallophanate.

5. The compound of claim 1 which is ethyl 4-(o-aminophenyl)-3-thioallophanate.

* * * * *